(12) United States Patent
Stacey et al.

(10) Patent No.: US 11,874,287 B2
(45) Date of Patent: Jan. 16, 2024

(54) AUTO-ALIGNING CABLE SENSOR

(71) Applicant: The Automation Partnership (Cambridge) Limited, Royston (GB)

(72) Inventors: Adrian Stacey, Cambridge (GB); Daren Huttlestone, Royston (GB); Edmund Grace, Cottenham (GB)

(73) Assignee: The Automation Partnership (Cambridge) Limited, Royston (GB)

( * ) Notice: Subject to any disclaimer, the term of this patent is extended or adjusted under 35 U.S.C. 154(b) by 774 days.

(21) Appl. No.: 17/040,908

(22) PCT Filed: Mar. 21, 2019

(86) PCT No.: PCT/EP2019/057092
§ 371 (c)(1),
(2) Date: Sep. 23, 2020

(87) PCT Pub. No.: WO2019/185445
PCT Pub. Date: Oct. 3, 2019

(65) Prior Publication Data
US 2021/0018523 A1    Jan. 21, 2021

(30) Foreign Application Priority Data

Mar. 27, 2018 (EP) .................................... 18164441

(51) Int. Cl.
*G01N 35/00* (2006.01)
*C12M 1/00* (2006.01)
*C12M 1/34* (2006.01)

(52) U.S. Cl.
CPC ....... *G01N 35/00584* (2013.01); *C12M 23/50* (2013.01); *C12M 41/36* (2013.01); *G01N 35/0099* (2013.01)

(58) Field of Classification Search
CPC ......... G01N 35/00584; G01N 35/0099; C12M 23/50; C12M 41/36; C12M 23/38
See application file for complete search history.

(56) References Cited

U.S. PATENT DOCUMENTS

| 2011/0111489 A1 | 5/2011 | Beese et al. |
| 2014/0234951 A1* | 8/2014 | Terentiev ............ B01F 33/4534 366/142 |

OTHER PUBLICATIONS

Extended European Search Report, EPO International Application No. 18164441.0-1111, dated Jul. 26, 2018, 8 pages.
(Continued)

*Primary Examiner* — David Z Huang
(74) *Attorney, Agent, or Firm* — Quarles & Brady LLP (57) ABSTRACT

An auto-aligning cable sensor for performing measurements on a medium contained in a vessel is provided. The cable sensor includes a cable which has an end sensor and which is adapted to be carried by a mounting fixture. The mounting fixture and the vessel are movable into a measurement position relative to each other such that a contact face of the end sensor is held in alignment against a surface of the vessel by a pressing force, thereby enabling the end sensor to sense a characteristic of the medium contained in the vessel. The cable sensor further includes an elastically deformable coupling member which is arranged to mediate transfer of the pressing force from the mounting fixture to the cable and thence to the end sensor when the mounting fixture and the vessel are moved into the measurement position. The coupling member deforms under the pressing force such that the cable can flex to tilt the end sensor relative to the surface of the vessel to accommodate misalignment of the contact face and the surface of the vessel.

15 Claims, 5 Drawing Sheets

(56) References Cited

OTHER PUBLICATIONS

International Preliminary Report on Patentability, PCT/EP2019/057092, dated Mar. 27, 2018, 6 pages.

* cited by examiner

AUTO-ALIGNING CABLE SENSOR

RELATED APPLICATIONS

This application is a 35 U.S.C. § 371 national phase application of PCT/EP2019/057092 (WO 2019/185445-A1), filed on Mar. 21, 2019, entitled "AUTO-ALIGNING CABLE SENSOR", which claims the benefit of EP Patent Application No. 18164441.0, filed Mar. 27, 2018, each of which are incorporated herein by reference in their entirety.

FIELD OF THE PRESENT DISCLOSURE

The present disclosure relates to the field of cable sensors for performing measurements on media contained in vessels, such as bioreactor vessels.

BACKGROUND

Cell culture is a process for growing cells in an artificial environment such as a bioreactor. Often, the cells are grown whilst suspended in a culture growth medium. Monitoring and/or controlling the environment to which the cells are exposed in the bioreactor is important in order to control the physiology of the cells and the amount of target produced. Specifically, the monitoring of various parameters of the cells and/or the culture growth medium within the bioreactor is key to their control.

Example bioreactor systems suitable for cell culture are described in US 2016/0152936 and WO 2014/020327.

Monitoring of parameters of the cells can be achieved invasively and/or non-invasively by measuring various characteristics of the cells. Invasive monitoring generally uses a sensor inserted directly into the culture growth medium contained in a vessel. In non-invasive monitoring, sensors are not placed in direct contact with the culture growth medium but may be positioned outside the vessel, for example.

An example of a characteristic of the cell culture which can be determined by measuring various parameters is biomass (i.e. the total quantity of cells in a given area or volume). There are many methods for determining biomass in liquid cultures, including dry cell weight, wet cell weight, and optical measurement (e.g. optical density or reflectance). For example U.S. Pat. No. 7,100,462 proposes a sensor which measures the reflectance (i.e. back-scattering) of incident light from the interior of a bioreactor, from which biomass can be determined.

Both optical and non-optical sensors can be used to measure biomass. Invasive sensors that can be immersed directly into the culture growth medium can be challenging to calibrate and have a high risk of cross-contamination between vessels. However, non-invasive probes located outside the vessel need to be arranged correctly in relation to the vessel in order to calibrate the sensor and also to provide accurate and consistent measurements in line with previous calibration. A consistent angular alignment and spacing of the sensor relative to the vessel can be difficult to achieve, particularly in the context of high-throughput, automated bioreactor systems where there is a requirement for simple, rapid, and reliable setup of multiple bioreactors for each experiment. Further considerations are that sensors should preferably be tolerant to moisture and should not degrade the sealing integrity of the system. Preferably also sensors should be simple to manufacture and compatible with existing bioreactors.

Therefore, a need exists for a sensor for performing measurements on a medium contained in a vessel which can be consistently aligned with the vessel in order to provide accurate and repeatable measurements.

SUMMARY

According to a first aspect of the disclosure, there is provided an auto-aligning cable sensor for performing measurements on a medium contained in a vessel, wherein the cable sensor includes:

a cable which has an end sensor and which is adapted to be carried by a mounting fixture, the mounting fixture and the vessel being movable into a measurement position relative to each other such that a contact face of the end sensor is held in alignment against a surface of the vessel by a pressing force, thereby enabling the end sensor to sense a characteristic of the medium contained in the vessel; and an elastically deformable coupling member which is arranged to mediate transfer of the pressing force from the mounting fixture to the cable and thence to the end sensor when the mounting fixture and the vessel are moved into the measurement position, the coupling member deforming under the pressing force such that the cable can flex to tilt the end sensor relative to the surface of the vessel to accommodate misalignment of the contact face and the surface of the vessel.

As the coupling member is deformable under the pressing force, the end sensor can automatically align itself with the surface of the vessel. The auto-aligning cable sensor is therefore able to correct for angular misalignment of the contact face relative to the surface of the vessel which may result from manufacturing deviations or incorrect assembly of the cable in the mounting fixture, for example. Indeed, the coupling member may also deform under the pressing force such that the sensor end can accommodate mis-spacing of the contact face and the surface of the vessel. The auto-aligning cable sensor may therefore enable faster and more accurate measurements on the medium contained in the vessel without the need for any additional components, while also allowing manufacturing tolerances for the vessel and the mounting fixture to be relaxed.

The auto-aligning cable sensor of the first aspect may have any one or any combination of the following optional features.

The cable may be able to flex to tilt the end sensor relative to the surface of the vessel to accommodate a misalignment of the contact face and the surface of the vessel of up to 3° in any direction, and preferably up to 5° in any direction.

The coupling member may be able to deform under the pressing force such that the sensor end can accommodate mis-spacing of the contact face and the surface of the vessel of up to ±0.5 mm, and preferably up to ±1 mm.

The elastically deformable coupling member may be carried by the cable adjacent the end sensor. Conveniently, the elastically deformable coupling member may be formed as a sleeve around the cable, an end of the sleeve abutting an abutment surface of the cable to transfer the pressing force to the cable. For example, the abutment surface may be the underside of a flange formed at the end of the cable. The top side of the flange can then be flush with the contact face. The flange may be formed by a ferrule at the end of the cable. The ferrule may be adhesion bonded (e.g. by epoxy resin) to the end of the cable to seal the ferrule to the end of the cable. This can prevent leaked and/or spilled liquid penetrating along an interface between the ferrule and the cable.

One of the end of the cable and the surface of the vessel may have a protrusion and the other of the end of the cable and the surface of the vessel may have matching bay that receives the protrusion when the contact face of the sensor end is held in alignment against the surface of the vessel by the pressing force, thereby preventing sideways motion of the end of the cable relative to the surface of the vessel. Advantageously, such an arrangement can improve measurement accuracies by reducing or eliminating slippage between the contact face and the surface of the vessel. The contact face may be located at the protrusion or the matching bay (as the case may be) of the end of the cable. Particularly when the cable has transmitting and receiving parts which both terminate at the contact face (e.g. a light emitting optical fibre and a light detecting optical fibre as discussed below), locating the contact face at the protrusion/bay allows the angle between the two parts and/or the distance in the sensed medium between them to be controlled.

The deformation of the coupling member under the pressing force typically seals, or improves a seal of, the coupling member to the cable (e.g. at such an abutment surface). For example, when the flange is formed by a ferrule at the end of the cable, the deformation of the coupling member under the pressing force can seal the coupling member to the ferrule. Accordingly, liquid penetration between the cable and the coupling member can also be prevented. Conveniently, the coupling member may be interference fitted to the cable in the coupling member's unloaded state (i.e. before application of the pressing force). In this case, the unloaded coupling member can already be sealed to the cable. The deformation of the coupling member under the pressing force may then improve this seal.

The coupling member may be formed from an elastomer, such as silicone. Such materials are suitably elastic and compliant, have good compatibility with bioreactor liquids, and can form tight seals.

The end sensor may sense an optical characteristic of the medium contained in the vessel. For example, the cable may include a light emitting optical fibre and a light detecting optical fibre which both terminate at the contact face for measuring optical density of a culture in the medium by scattered light. For such measurements to be accurately and repeatedly performed, consistently correct angular alignment and positioning of the contact face relative to the vessel surface is important. The auto-aligning cable sensor can provide this consistency. However, with a suitably adapted end sensor, other possibilities for the cable sensor are the detection of acoustic, electromagnetic or other optical properties of the medium contained in the vessel.

According to a second aspect of the disclosure, there is provided a measurement apparatus for performing measurements on a medium contained in a vessel, the system including:

the auto-aligning cable sensor according to the first aspect; and a mounting fixture carrying the cable sensor, the mounting fixture and the vessel being movable into a measurement position relative to each other such that the contact face of the end sensor is held in alignment against a surface of the vessel by a pressing force to sense a characteristic of the medium contained in the vessel, and such that the coupling member mediates transfer of the pressing force from the mounting fixture to the cable and thence to the end sensor end when the mounting fixture and the vessel are moved into the measurement position.

The measurement apparatus of the second aspect may have any one or any combination of the following optional features.

Conveniently, the mounting fixture may be a base for supporting the vessel, the mounting fixture and the vessel being movable into the measurement position by locating the vessel on the base. Some or all of the pressing force can thus be provided by the weight of the vessel acting on the base.

The deformation of the coupling member under the pressure force may seal, or may improve a seal of, the coupling member to the mounting fixture. Accordingly, the penetration of liquid between the coupling member and the mounting fixture can also be prevented. As the coupling member also typically seals to the cable (as discussed above), the auto-aligning sensor can therefore help to prevent the spread of liquid spills. Conveniently, the coupling member may be interference fitted to the mounting fixture in the coupling member's unloaded state (i.e. before application of the pressing force). In this case, the unloaded coupling member can already be sealed to the mounting fixture. The deformation of the coupling member under the pressing force may then improve this seal.

The elastically deformable coupling member may abut an abutment surface of the mounting fixture to transfer the pressing force from the mounting fixture to the coupling member (and typically also seal the coupling member to the mounting fixture). As an example, when the elastically deformable coupling member is formed as a sleeve around the cable (as discussed above), the other end of the sleeve can abut the abutment surface of the mounting fixture. The cable sensor may be threaded through a hole formed in the mounting fixture, the hole being configured to allow the cable to flex therein to tilt the end sensor relative to the surface of the vessel, and the hole having a shoulder which forms the abutment surface of the mounting fixture.

According to a third aspect of the disclosure, there is provided a bioreactor for fermentation or cell culture having one or more bioreactor vessels and one or more respective measurement apparatuses according to the second aspect for performing measurements on media contained in the, or each, bioreactor vessel.

The bioreactor of the third aspect may have any one or any combination of the following optional features.

When the mounting fixture and the vessel are in the measurement position relative to each other, the end sensor may locate in a recess formed in a wall of the vessel such that the contact face is held in alignment against a bottom surface of the recess.

The bioreactor may have a robotic manipulator for moving the, or each, bioreactor vessel into the measurement position.

According to a fourth aspect of the disclosure, there is provided a method for performing measurements on a medium contained in a vessel, the method including the steps of:

providing the measurement apparatus according to the second aspect;

moving the mounting fixture and the vessel into a measurement position relative to each other such that the contact face of the end sensor is held in alignment against a surface of the vessel by a pressing force, and such that the coupling member mediates transfer of the pressing force from the mounting fixture to the cable and thence to the end sensor, the coupling member deforming under the pressing force such that the cable can flex to tilt the end sensor relative to the surface of the vessel to accommodate misalignment of the contact face and the surface of the vessel; and using the aligned contact face to sense a characteristic of the medium contained in the vessel.

The method may be performed using the bioreactor of the third aspect.

BRIEF DESCRIPTION OF THE DRAWINGS

Embodiments of the present disclosure will now be described by way of example with reference to the accompanying drawings in which.

DETAILED DESCRIPTION

Figure 1:
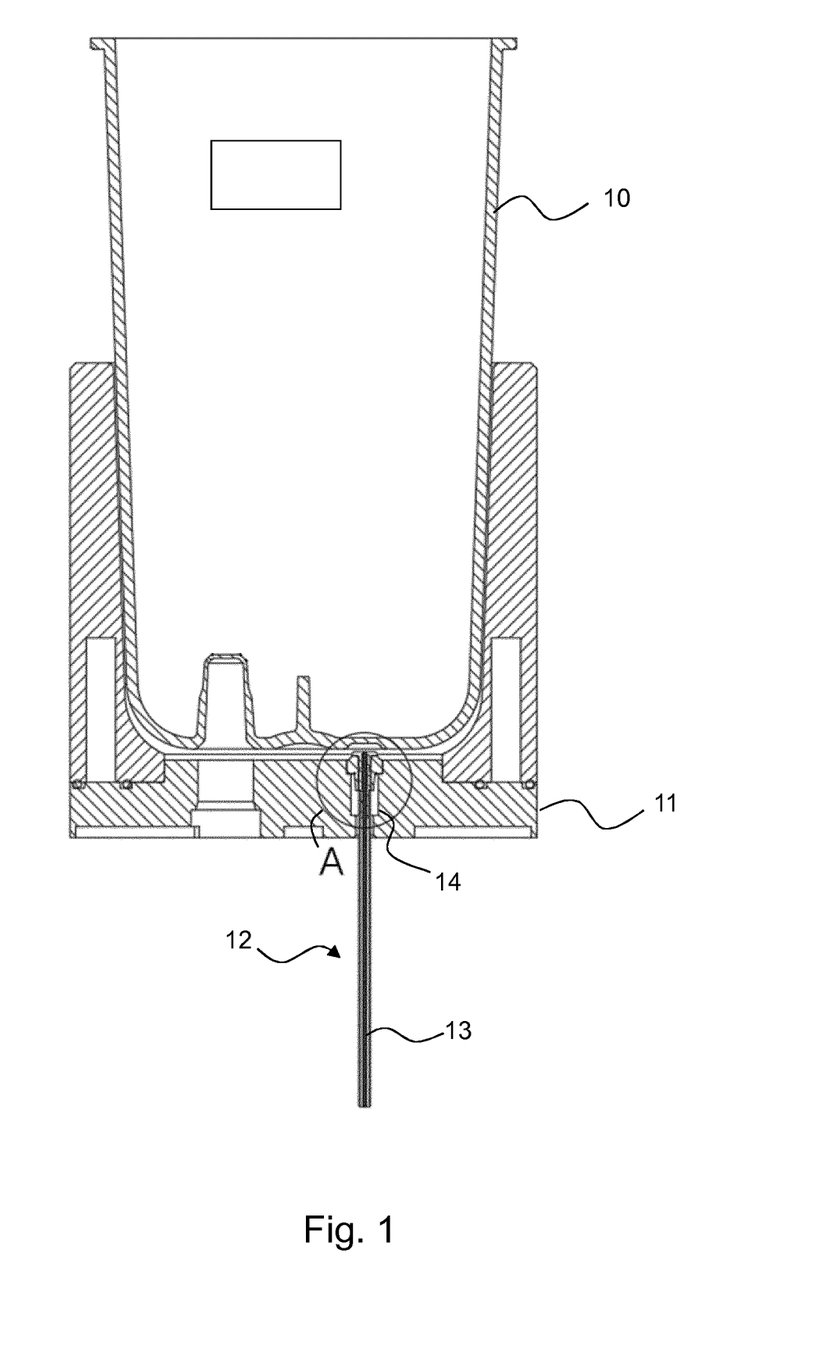
FIG. 1 shows a cross section through a bioreactor vessel located on a support base.

FIG. 1 shows a cross section through a clear-sided bioreactor vessel 10 located on a support base 11. For example, the vessel 10 can be a modular vessel of a high throughput bioreactor system such as the Ambr™ 250 system available from Sartorius Stedim Systems GmbH. This system enables automated media fill, inoculation, sampling and feeding, with individual measurement and control for each bioreactor vessel of parameters of interest such as temperature, impeller speed, pH and dissolved oxygen.

The support base 11 provides a convenient mounting fixture for non-invasive sensors used to monitor parameters of the medium within the vessel 10. In particular, FIG. 1 shows the support base carrying a cable sensor 12 having a cable 13 which threads through a hole 14 formed in the base 11 to end in a sensor contact face 15 which presses against an external sensing surface 16 of the vessel, as shown in more detail in FIGS. 2A and 2B, which are detailed views of region A of FIG. 1 respectively before and after location of the vessel 10 on the base 11. The sensing surface 16 is formed at the base of a recess in the wall of the vessel 10.

Figure 2A:
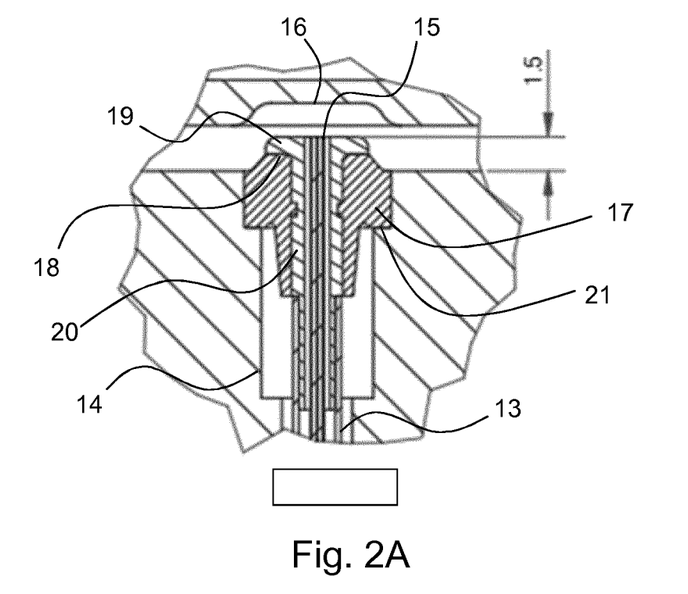
FIG. 2A shows detail of region A of FIG. 1 before the vessel is located on the base.
Figure 2B:
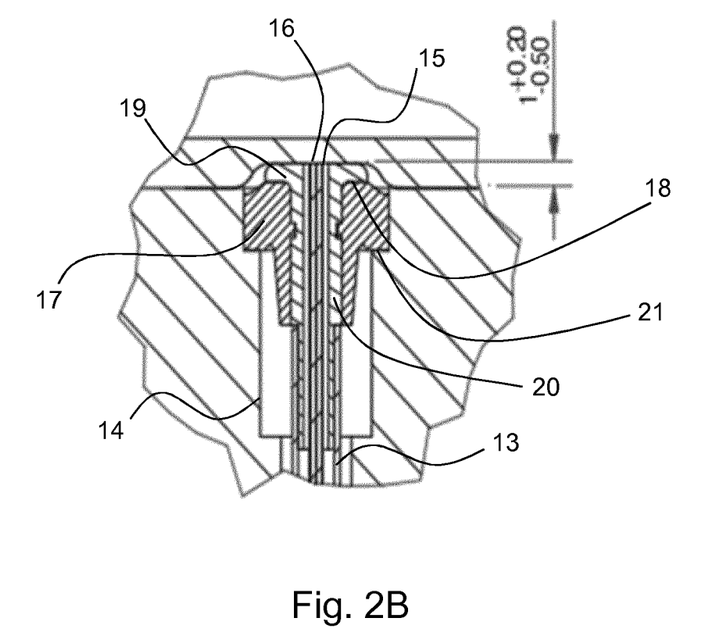
FIG. 2B shows detail of region A of FIG. 1 after the vessel is located on the base.

The cable sensor 12 is used to measure a further parameter of interest, such as optical reflectance, from which biomass can be inferred. To this end, the cable 13 contains two optical fibres: one to transmit light to the contact face 15 and from there to emit the light through the bottom of the vessel at the sensing surface 16 and into the medium, and the other to receive back-scattered light from the medium which has returned to the contact face 15 and to transmit the light to a suitable signal processing unit. The light may be infrared light, for example. For this measurement to be performed accurately and repeatably it is critical that the contact face 15 is aligned completely flat against the sensing surface 16 so that the two optical fibres are correctly positioned relative to each other and the sensing surface 16. A problem arises however that, due to equipment tolerances and robotic handling variations, the angle of the sensing surface 16 relative to the support base 11 can vary within a range of a few degrees when the vessel 10 is located on the base 11. Moreover for similar reasons the spacing of the sensing surface 16 from the support base 11 can vary within a range of several hundreds of microns. Thus if the orientation and location of the contact face 15 were solely determined by the orientation and location of the support base 11 relative to the sensing surface 16, this would have a deleterious effect on the reflectance measurements.

Accordingly, the cable sensor 12 includes an elastically deformable coupling member 17, conveniently configured as a sleeve interference fitted around the cable 13. In particular, the coupling member 17 can be formed of an elastomer such as silicone, which combines toughness and resilience with chemical inertness so that it is not easily damaged during operation, maintenance or cleaning of the system. Alternative embodiments of the cable sensor could have different forms of coupling member, such as an arrangement of one or more springs positioned around the cable 13. However, an elastomeric coupling member can provide particular advantages in respect of sealing and moisture tolerance.

As shown in FIGS. 2A and 2B, a ferrule 20 is provided at the end of the cable 13, and the coupling member 17 encircles the ferrule 20. In this way, the coupling member 17 abuts an abutment surface 18, which is the underside of a flange 19 formed by the ferrule, the top side of the flange 19 being flush with the contact face 15. The ferrule 20 is adhesion bonded (e.g. by epoxy resin) to the cable 13 to form a fluid tight seal. The ferrule 20 has a low compressibility, and may be formed from polyether ether ketone (PEEK), for example.

The hole 14 in the support base 11 through which the cable 13 is threaded is sized to allow the cable 13 to move laterally within the hole 14 such that the cable 13 can flex. The coupling member 17 acts as a bung by interference fitting within a larger diameter portion of the hole 14, the coupling member being supported on a shoulder 21 of the support base 11 where the hole 14 reduces in diameter. Accordingly, one end of the coupling member 17 abuts the underside of the flange 19, the opposite end of the coupling member 17 abuts the shoulder 21. The interference fits of the coupling member 17 around the stem of the ferrule 20 and within the larger diameter portion of the hole 14, supplemented by the abutment with the underside of the flange 19 and the shoulder 21, can form a fluid tight seal between the ferrule 20 and the support base 11 even before the coupling member 17 is compressed (as discussed below). Accordingly, leaked and/or spilled liquid (from the vessel 10, or otherwise) can be prevented from penetrating through the hole 14.

The location of the vessel 10 on the base 11, shown in FIG. 2B, moves the vessel 10 into a measurement position relative to the base 11, such that the sensor contact face 15 is held by a pressing force in alignment against the sensing surface 16 of the vessel 10. In particular, the reaction of the base 11 to the weight of the vessel 10 generates the pressing force, which is transmitted from the shoulder 21, through the coupling member 17, to the underside of the flange 19, and thence to the contact face 15. If necessary, the pressing force may be augmented by a suitable clamping mechanism (not illustrated) used to clamp the vessel 10 to the support base 11.

The coupling member 17 enables the cable sensor 12 to auto-align to accommodate mis-orientation and mis-spacing of the contact face 15 and the sensing surface 16 due to, for example, manufacturing deviations, equipment tolerances and/or robotic handling variations.

Figure 3:
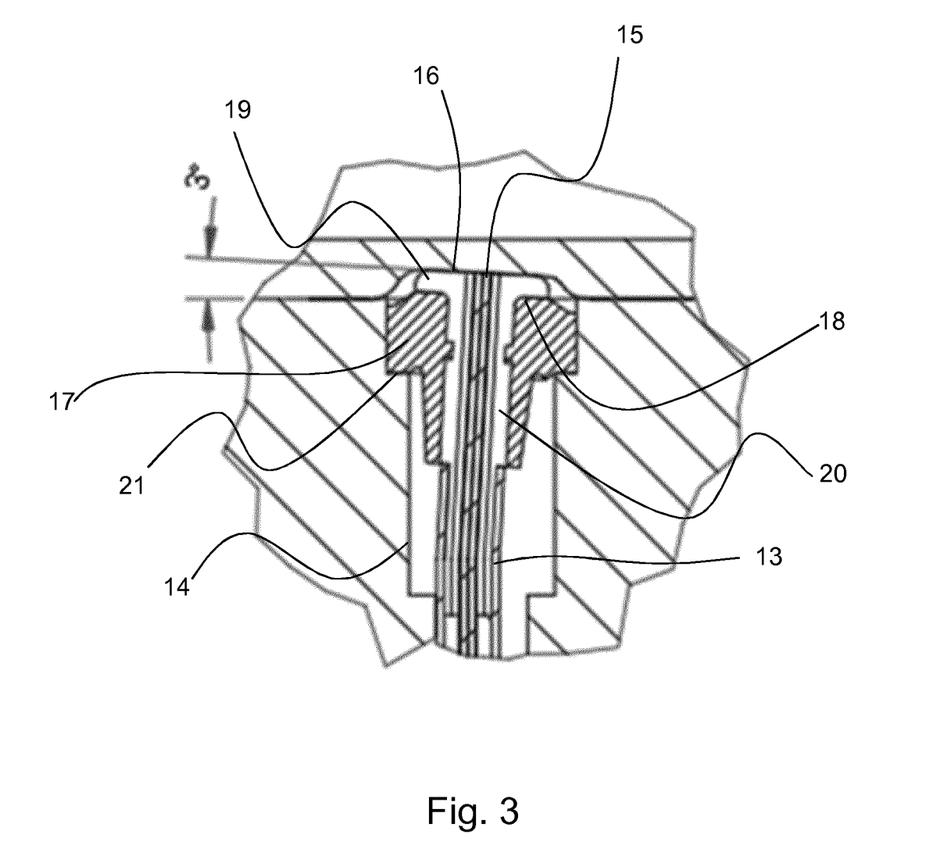
FIG. 3 shows detail of region A of FIG. 1 after the vessel is located on the base in a scenario where a sensing surface of the vessel is angled due to low tolerance in manufacture of the vessel.

Specifically, the coupling member 17 deforms under the pressing force to automatically align the contact face 15 to the sensing surface 16. As shown in FIG. 3, the cable sensor 12 is therefore able to correct for angular misalignment of the contact face 15 relative to the sensing surface 16 of e.g. up to about 3° in any direction, and preferably up to about 5° in any direction. The coupling member 17 may also correct mis-spacings of the contact face 15 relative to the sensing surface 16 of e.g. up to about ±0.5 mm, and preferably up to about ±1 mm. In this way, the contact face 15 can be made to lie completely flat against the sensing surface 16, enabling fast and accurate reflectance measurements.

The deformation of the coupling member 17 under the pressing force also improves the sealing of the coupling member 17 to the shoulder 21 of the base 11 and the underside of the flange 19. Moreover, the pressing force compresses the coupling member in the axial direction of the cable 13, which in turn increases its tightness of fit against the sidewalls of the hole 14 and the stem of the ferrule 20 to improve its sealing to these surfaces.

Figure 4:
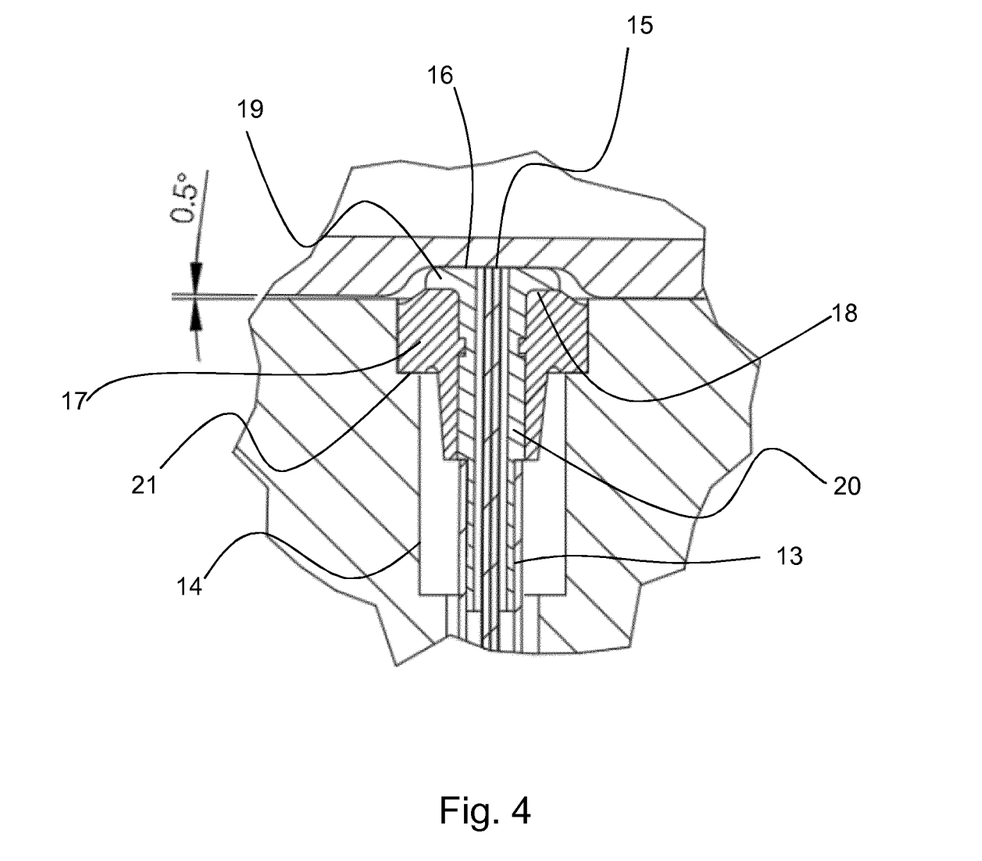
FIG. 4 shows another detail of region A of FIG. 1 after the vessel is located on the base in a scenario where a sensing surface of the vessel is angled due to poor tolerance in manufacture of the vessel.

In FIG. 3, the sensing surface 16 of the vessel 10 is angled due to low tolerance in manufacture of the vessel. FIG. 4 shows another detail of region A of FIG. 1 after the vessel 10 is located on the base 11 in a scenario where the vessel is manufactured to a better tolerance but is imperfectly positioned such that the entire vessel is angled (by 0.5° as illustrated) relative to the base. This results in the sensing surface 16 being angled by a similar amount relative to the base. However, once again the coupling member 17 deforms under the pressing force to automatically align the contact face 15 to the angled sensing surface 16.

In summary, the coupling member 17 operates to automatically align the sensor contact face 15 with the sensing surface 16. Specifically, the coupling member 17 deforms under the pressing force, so that the cable 13 flexes thereby tilting the end sensor and bringing the contact face 15 into correct alignment. Advantageously the coupling member 17 can also correct for mis-spacings between the contact face 15 and the sensing surface 16, and can help to prevent spread of leaked or spilled liquid. No tools are required for insertion or adjustment of the base 11 position in order to achieve these effects. In order to perform measurements of the medium contained in the vessel 10, a human operator or robotic manipulator of the bioreactor system simply moves the vessel 10 and/or support base 11 into the measurement position relative to each other such that the sensor contact face 15 is held against the sensing surface 16 under the pressing force, and then uses the contact face 15 to sense a characteristic of the medium contained in the vessel 10.

Although the above example of the auto-aligning cable sensor 12 senses optical reflectance, other characteristics of the medium contained in the vessel 10 can be measured by such a sensor. For example, the sensor may be used to excite and receive measurements from an optically activatable spot in the base of the vessel to response to medium features such as pH, dissolved oxygen, etc. The cable sensor 12 may additionally/alternatively be adapted to measure acoustic or electromagnetic properties of the medium. Thus the cable may carry electrical wires instead of optical fibres. For example, a conductive element in the wall of the vessel may be used, for example, for impedance-based measurements, or the vessel may include a coupling mechanism for capacitance sensing. Efficient and reliable coupling, such as that enabled by the auto-aligning cable sensor described above, is generally critical for accurate and low-noise measurements using such techniques. Also, although described above in relation to a bioreactor vessel 10, the auto-aligning cable sensor 12 may be used for interrogating other types of vessels, such as mixing tanks or pipework.

In the above example, the sensing surface 16 is conveniently a flat surface at the base of the recess in the wall of the vessel 10. A potential problem with this arrangement, however, is that under some circumstances the sensor contact face 15 can slip sideways, which may affect measurement accuracies by the cable sensor 12. One option to address this problem is to make the topside of the flange 19 a closer match to the shape of the recess which provides the sensing surface 16. The flange 19 can then be more closely contained in the recess to limit or prevent sideways slippage, while the deformability of the coupling member 17 can ensure that the flange 19 is guided into the recess on location of the vessel 10 on the base 11. Another option is to improve the frictional resistance between the topside of the flange and the sensing surface 16.

Figure 5A:
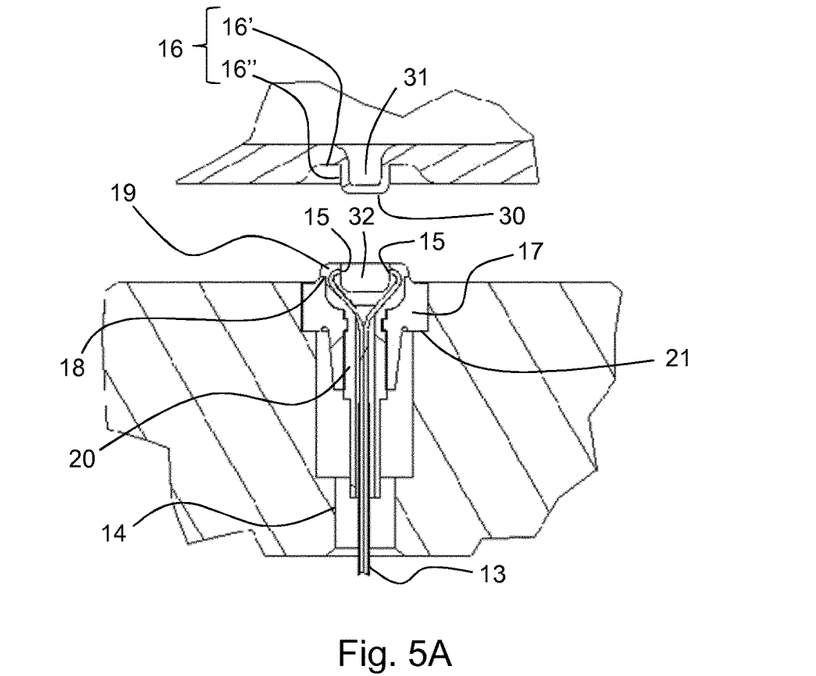
FIG. 5A shows detail of a region corresponding to region A for a variant and cable sensor before the vessel is located on the base.
Figure 5B:
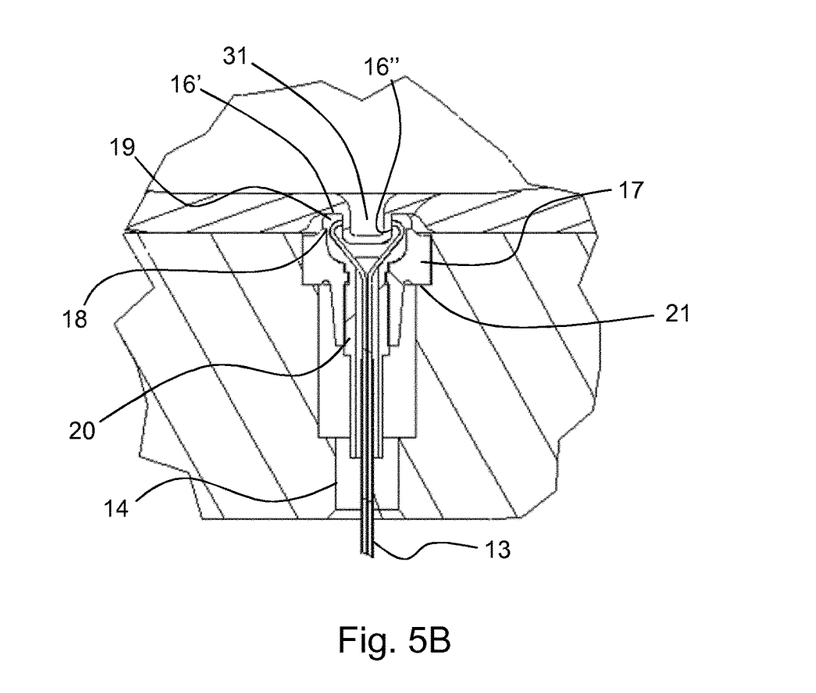
FIG. 5B shows detail of the region A of FIG. 5A after the variant vessel is located on the base.

FIG. 5A shows detail of a region corresponding to region A for a variant arrangement of the vessel 10 and the cable sensor 12 before the vessel is located on the base 11, and FIG. 5B shows detail of the same region after the variant vessel is located on the base. In the variant, the sensing surface 16 has a radially outer, annular first portion 16' which is a flat surface at the base of the recess in the wall of the vessel. A thin-walled, cylindrical protrusion 30 at the centre of the recess then forms a projecting second portion 16" of the sensing surface 16 radially inside the annular first portion. As explained in more detail below, the thin-walled protrusion is dual purpose: it serves to anchor the end of the cable sensor 12 against sideways movement, and it also forms a defined space 31 within the vessel for interrogation by the cable sensor.

Matching the protrusion 30, the ferrule 20 has a central, cylindrical bay 32 which is sized to receive the protrusion 30 so that encircling sides of the bay slidingly engage with the second portion 16" of the sensing surface when the vessel 10 is located on the base 11, the deformability of the coupling member 17 ensuring that the protrusion 30 docks properly with the bay. More particularly, in the event of initial axial misalignment of the protrusion and the bay, curved edges around the leading face of the protrusion exert a sideways force on the ferrule at the mouth of the bay which deforms the coupling member so that the ferrule can deflect sideways to bring the protrusion and the bay into sufficient alignment to allow the protrusion to insert into the bay. Further movement of the vessel onto the base 11 brings the topside of the flange 19 into abutment with the annular first portion 16' of the sensing surface such that the topside is held by the pressing force produced by the weight of the vessel in alignment against the first portion 16' of the sensing surface. This perfects the alignment of the protrusion in the bay. The engaged protrusion and bay effectively eliminate the possibility of sideways slippage of the end of the cable sensor 12 relative to the sensing surface.

The cable 13 again contains two optical fibres: one to transmit light into the medium in the vessel and the other to receive light from the medium in the vessel. However, the central bay 32 allows the fibres to curve around to opposite sides of the bay and arrive at the side wall of the bay aligned substantially perpendicularly thereto. The sensor contact face 15 is thus formed in two opposing parts facing each other across the bay. This arrangement allows the receiving fibre to sense variation, e.g. due to absorbance, in the light sent by the transmitting fibre across the medium in the interrogation space 31 formed by the protrusion 30, rather than to sense back-scattered light.

In further variants, the protrusion 30 and the matching bay 32 may have other shapes. For example they may be hemispherical or frustoconical. Such different shapes allow the angle between the two fibres when they arrive at the sensor contact face 15 to be varied, such that the sensor can detect different relative amounts of transmitted and back-scattered light in the interrogation space 31.

Indeed, particularly if the cable carries electrical wires instead of optical fibres and it is desired to increase the distance in the medium between the ends of the wires (e.g. to increase the impedance or capacitance of the medium between the ends of the wires), the ferrule may have a protrusion which is received into a matching bay of the wall of the vessel 10, with the matching bay in turn protruding into the interior of the vessel. The ends of the wires can then be directed outwards from each other on opposite sides of the protrusion to increase the sensed distance in the medium therebetween.

In yet further variants, the sensor contact face 15 may be located on the topside of the flange 19 at a different part of the ferrule to a protrusion or matching bay formed therein. Thus in this case the protrusion or matching bay serves purely to anchor the end of the cable sensor against sideways movement.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Moreover, in determining extent of protection, due account shall be taken of any element which is equivalent to an element specified in the claims. Various changes to the described embodiments may be made without departing from the spirit and scope of the invention.

All references referred to above are hereby incorporated by reference.

The invention claimed is:

1. An auto-aligning cable sensor for performing measurements on a medium contained in a vessel, wherein the cable sensor includes:
   a cable which has an end sensor and which is adapted to be carried by a mounting fixture, the mounting fixture and the vessel being movable into a measurement position relative to each other such that a contact face of the sensor end is held in alignment against a surface of the vessel by a pressing force, thereby enabling the end sensor to sense a characteristic of the medium contained in the vessel; and
   an elastically deformable coupling member which is arranged to mediate transfer of the pressing force from the mounting fixture to the cable and thence to the end sensor when the mounting fixture and the vessel are moved into the measurement position, the coupling member deforming under the pressing force such that the cable can flex to tilt the end sensor relative to the surface of the vessel to accommodate misalignment of the contact face and the surface of the vessel.

2. The auto-aligning cable sensor according to claim 1, wherein the elastically deformable coupling member is formed as a sleeve around the cable, an end of the sleeve abutting an abutment surface of the cable to transfer the pressing force to the cable.

3. The auto-aligning cable sensor according to claim 2, wherein the abutment surface is the underside of a flange formed at the end of the cable.

4. The auto-aligning cable sensor according to claim 3, wherein the top side of the flange is flush with the contact face.

5. The auto-aligning cable sensor according to claim 3, wherein the flange is formed by a ferrule at the end of the cable.

6. The auto-aligning cable sensor according to claim 1, wherein one of the end of the cable and the surface of the vessel has a protrusion and the other of the end of the cable and the surface of the vessel has matching bay that receives the protrusion when the contact face of the sensor end is held in alignment against the surface of the vessel by the pressing force, thereby preventing sideways motion of the end of the cable relative to the surface of the vessel.

7. The auto-aligning cable sensor according to claim 6, wherein the contact face is located at the protrusion or the matching bay of the end of the cable.

8. A measurement apparatus for performing measurements on a medium contained in a vessel, the system including:
   the auto-aligning cable sensor of claim 1; and
   a mounting fixture carrying the cable sensor, the mounting fixture and the vessel being movable into a measurement position relative to each other such that the contact face of the end sensor is held in alignment against a surface of the vessel by a pressing force to sense a characteristic of the medium contained in the vessel, and such that the coupling member mediates transfer of the pressing force from the mounting fixture to the cable and thence to the end sensor when the mounting fixture and the vessel are moved into the measurement position.

9. The measurement apparatus according to claim 8, wherein the mounting fixture is a base for supporting the vessel, the mounting fixture and the vessel being movable into the measurement position by locating the vessel on the base.

10. The measurement apparatus according to claim 8, wherein the deformation of the coupling member under the pressing force seals, or improves a seal of, the coupling member to the mounting fixture.

11. The measurement apparatus according to claim 8, wherein the elastically deformable coupling member abuts an abutment surface of the mounting fixture to transfer the pressing force from the mounting fixture to the coupling member.

12. The measurement apparatus according to claim 11, wherein the cable sensor is threaded through a hole formed in the mounting fixture, the hole being configured to allow the cable to flex therein to tilt the end sensor relative to the surface of the vessel, and the hole having a shoulder which forms the abutment surface of the mounting fixture.

13. A bioreactor system for fermentation or cell culture having one or more bioreactor vessels and one or more respective measurement apparatuses according to claim 8 for performing measurements on media contained in the, or each, bioreactor vessel.

14. The bioreactor system according to claim 13, further having a robotic manipulator for moving the, or each, bioreactor vessel into the measurement position.

15. A method for performing measurements on a medium contained in a vessel, the method including the steps of:
- providing the measurement apparatus of claim 8;
- moving the mounting fixture and a vessel into a measurement position relative to each other such that the contact face of the end sensor is held in alignment against a surface of the vessel by a pressing force, and such that the coupling member mediates transfer of the pressing force from the mounting fixture to the cable and thence to the end sensor, the coupling member deforming under the pressing force such that the cable can flex to tilt the end sensor relative to the surface of the vessel to accommodate misalignment of the contact face and the surface of the vessel; and
- using the aligned contact face to sense a characteristic of the medium contained in the vessel.

* * * * *